United States Patent [19]

Bundy et al.

[11] 4,051,160
[45] Sept. 27, 1977

[54] CIS-4,5-DIDEHYDRO-11-DEOXY-13,14-DIHYDRO-PG COMPOUNDS

[75] Inventors: Gordon L. Bundy, Kalamazoo; Norman A. Nelson, Galesburg, both of Mich.

[73] Assignee: The Upjohn Company, Kalamazoo, Mich.

[21] Appl. No.: 648,268

[22] Filed: Jan. 12, 1976

Related U.S. Application Data

[62] Division of Ser. No. 548,586, Feb. 10, 1975, Pat. No. 3,987,072.

[51] Int. Cl.$^2$ .............................................. C07C 177/00
[52] U.S. Cl. .............................. 260/413; 260/410.9 R; 260/514 D; 560/121
[58] Field of Search ............. 260/410.9 R, 413, 514 D, 260/468 D

[56] References Cited

U.S. PATENT DOCUMENTS 3,917,668  11/1975  Abraham et al. .................... 260/468

*Primary Examiner*—Robert Gerstl
*Attorney, Agent, or Firm*—Robert A. Armitage

[57] ABSTRACT

This invention relates to a group of cis-4,5-didehydro-11-deoxy-$PG_1$ analogs having variable chain length, optional methyl substitution in the methyl-terminated side-chain, and processes for making them. These compounds are useful for a variety of pharmacological purposes, including ulcer treatment, inhibition of platelet aggregation, increase of nasal patency, and labor induction at term.

40 Claims, No Drawings

CIS-4,5-DIDEHYDRO-11-DEOXY-13,14-DIHYDRO-PG COMPOUNDS

This application is a division of Ser. No. 548,586, filed Feb. 10, 1975, now issued as U.S. Pat. No. 3,987,072.

The present invention relates to prostaglandin analogs, for which the essential material constituting a disclosure thereof is incorporated by reference here from U.S. Pat. No. 3,987,072, issued Oct. 19, 1976.

We claim:

1. A compound of the formula

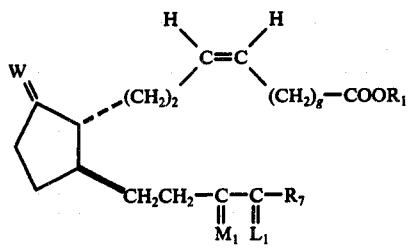

or a mixture comprising that compound and the enantiomer thereof;

wherein W is

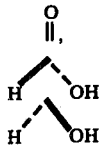

wherein $g$ is 2 to 4, inclusive;
wherein $L_1$ is

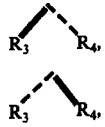

or

or a mixture of

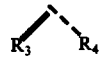

and

wherein $R_3$ and $R_4$ are hydrogen or methyl, being the same or different,
wherein $M_1$ is

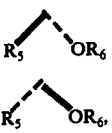

wherein $R_5$ and $R_6$ are hydrogen or methyl, with the proviso that $R_5$ is methyl only when $R_6$ is hydrogen and $R_6$ is methyl only when $R_5$ is hydrogen;

wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, 2, or 3 chloro or alkyl of one to 4 carbon atoms, inclusive, or a pharmacologically acceptable cation; and wherein $R_7$ is $-(CH_2)_m-CH_3$, wherein $m$ is one to 5, inclusive.

2. A compound according to claim 1, wherein W is

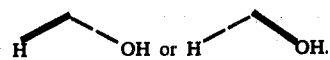

3. A compound according to claim 2, wherein W is

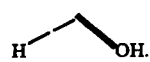

4. A compound according to claim 2, wherein W is

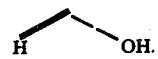

5. A compound according to claim 1, wherein W is

6. A compound according to claim 5, wherein $M_1$ is

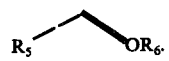

7. A compound according to claim 5, wherein $M_1$ is

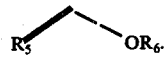

8. A compound according to claim 7, wherein $m$ is 3.
9. A compound according to claim 8, wherein $g$ is 4.
10. A compound according to claim 9, wherein $R_3$ is hydrogen and $R_4$ is methyl.
11. A compound according to claim 9, wherein $R_3$ and $R_4$ are methyl.
12. A compound according to claim 11, wherein $R_5$ is methyl.
13. A compound according to claim 11, wherein $R_6$ is methyl.
14. A compound according to claim 11, wherein $R_5$ and $R_6$ are hydrogen.
15. 2a,2b-Dihomo-cis-4,5-didehydro-11-deoxy-16,16-dimethyl-13,14-dihydro-PGE$_1$, a compound according to claim 14.
16. A compound according to claim 9, wherein $R_3$ and $R_4$ are hydrogen.
17. A compound according to claim 16, wherein $R_5$ and $R_6$ are hydrogen.
18. A compound according to claim 16, wherein $R_6$ is methyl.
19. A compound according to claim 16, wherein $R_5$ is methyl.
20. 2a,2b-Dihomo-cis-4,5-didehydro-11-deoxy-15-methyl-13,14-dihydro-PGE$_1$, a compound according to claim 19.
21. A compound according to claim 8, wherein $g$ is 2.
22. A compound according to claim 21, wherein $R_3$ is methyl and $R_4$ is hydrogen.
23. A compound according to claim 22, wherein $R_5$ and $R_6$ are both hydrogen.

24. Cis-4,5-Didehydro-11-deoxy-16-methyl-13,14-dihydro-PGE$_1$, a compound according to claim 23.

25. A compound according to claim 19, wherein R$_3$ and R$_4$ are hydrogen.

26. A compound according to claim 25, wherein R$_5$ and R$_6$ are hydrogen.

27. Cis-4,5-Didehydro-11-deoxy-13,14-dihydro-PGE$_1$, a compound according to claim 26.

28. A compound according to claim 25, wherein R$_6$ is methyl.

29. Cis-4,5-Didehydro-11-deoxy-13,14-dihydro-PGE$_1$, 15-methyl ether, a compound according to claim 28.

30. A compound according to claim 25, wherein R$_5$ is methyl.

31. Cis-4,5-Didehydro-11-deoxy-15-methyl-13,14-dihydro-PGE$_1$, a compound according to claim 30.

32. Cis-4,5-Didehydro-11-deoxy-15-methyl-13,14-dihydro-PGE$_1$, methyl ester, a compound according to claim 30.

33. A compound according to claim 31, wherein R$_3$ and R$_4$ are methyl.

34. A compound according to claim 33, wherein R$_5$ and R$_6$ are hydrogen.

35. Cis-4,5-Didehydro-11-deoxy-16,16-dimethyl-13,14-dihydro-PGE$_1$, a compound according to claim 34.

36. Cis-4,5-Didehydro-11-deoxy-16,16-dimethyl-13,14-dihydro-PGE$_1$, methyl ester, a compound according to claim 35.

37. A compound according to claim 33, wherein R$_5$ is methyl.

38. Cis-4,5-Didehydro-11-deoxy-15-methyl-16,16-dimethyl-13,14-dihydro-PGE$_1$, a compound according to claim 27.

39. A compound according to claim 33, wherein R$_6$ is methyl.

40. Cis-4,5-Didehydro-11-deoxy-16,16-dimethyl-13,14-dihydro-PGE$_1$, 15-methyl ether, a compound according to claim 39.

* * * * *